United States Patent [19]

Yasushi

[11] Patent Number: 5,191,894
[45] Date of Patent: Mar. 9, 1993

[54] BRAIN WAVE INDUCING APPARATUS
[75] Inventor: Mitsuo Yasushi, Saitama, Japan
[73] Assignee: Pioneer Electronic Corporation, Tokyo, Japan
[21] Appl. No.: 833,936
[22] Filed: Feb. 11, 1992
[30] Foreign Application Priority Data
May 28, 1991 [JP] Japan .................................. 3-123687
[51] Int. Cl.$^5$ ............................................. A61B 5/04
[52] U.S. Cl. ................................................... 128/733
[58] Field of Search ...................... 128/732; 600/26-28
[56] References Cited

U.S. PATENT DOCUMENTS 5,036,858  8/1991  Carter et al. ........................ 128/732

FOREIGN PATENT DOCUMENTS 0375106  6/1990  European Pat. Off. ............ 128/732

*Primary Examiner*—Max Hindenburg
*Attorney, Agent, or Firm*—Sughrue, Mion, Zinn, Macpeak & Seas

[57] ABSTRACT

A band pass filter has a center frequency that may be changed for scanning or sweeping across a frequency range of a desired brain wave to pass selected frequency components of the brain wave. A brain wave amplitude calculator calculates and stores therein the amplitude of the output of the band pass filter for each value of center frequency of the band pass filter. An optimum frequency calculator calculates and outputs a command indicative of an optimum center frequency of the band pass filter on the basis of the respective center frequencies and their amplitudes. A center frequency selector changes the center frequency of the band pass filter in accordance with the command.

17 Claims, 3 Drawing Sheets

BRAIN WAVE INDUCING APPARATUS

BACKGROUND OF THE INVENTION

1. Field of the Invention

The present invention relates to a brain wave inducing apparatus where the brain waves of a testee are picked up by a brain wave sensor and are subjected to filtering and converted into an optical signal which in turn is fed back to the testee so as to induce a specific brain wave.

2. Related Art

It is well known that there is a close relationship between the brain waves of man and his biological, psychological effects. For example, when a person is relaxed, the α wave (about 8–13 Hz) is dominantly developed. When the person is mentally and physically active, the β wave (about 14–30 Hz) is dominant. When the person feels sleepy, the θ wave (about 4–7 Hz) is dominant.

Conversely, if a specific brain wave is induced dominantly, then the person will enter the corresponding physical and psychological condition.

Therefore, the use of the relationship between these brain waves and physical and psychological conditions may be useful in controlling physical and psychological conditions of human beings. For example, a testee is given an external optical stimulation so as to induce α waves to direct the testee to a relaxed condition, so that the testee is relieved from stress or acquires a psychological concentration. Conventional brain wave inducing apparatuses for such purposes were such that the brain wave of a testee picked up through a brain wave sensor is converted into an optical signal and fed back to the testee for optical stimulation. However, direct conversion from brain waves into optical signals is has not been efficient in inducing specific brain waves.

SUMMARY OF THE INVENTION

An object of the invention is to provide a brain wave inducing apparatus where the brain waves of a testee are first subjected to filtering to determine the optimum frequency of a brain wave inducing signal and the testee is optically stimulated by the use of the brain wave inducing signal having a specific band width with the optimum frequency in the center of the band width. This allows efficient induction of brain waves of a testee.

A band pass filter has a center frequency that may be changed to scan or sweep across a frequency range of brain waves to pass selected frequency components of brain waves. The output of the band pass filter is supplied to a brain wave amplitude calculator which calculates and stores therein the amplitudes of the outputs for each of the center frequencies. An optimum frequency calculator performs a calculation on the basis of the respective center frequencies and their amplitudes from the brain wave amplitude calculator, and outputs a command indicative of an optimum center frequency of band pass filter. A center frequency selector changes the center frequency of the band pass filter in accordance with the command from the optimum frequency calculator.

BRIEF DESCRIPTION OF THE DRAWINGS

Features and other objects of the invention will be more apparent from the description of the preferred embodiment with reference to the accompanying drawings in which.

DETAILED DESCRIPTION OF THE PREFERRED EMBODIMENTS

Embodiment

An embodiment of the invention will now be described in detail with reference to the drawings.

Figure 1:
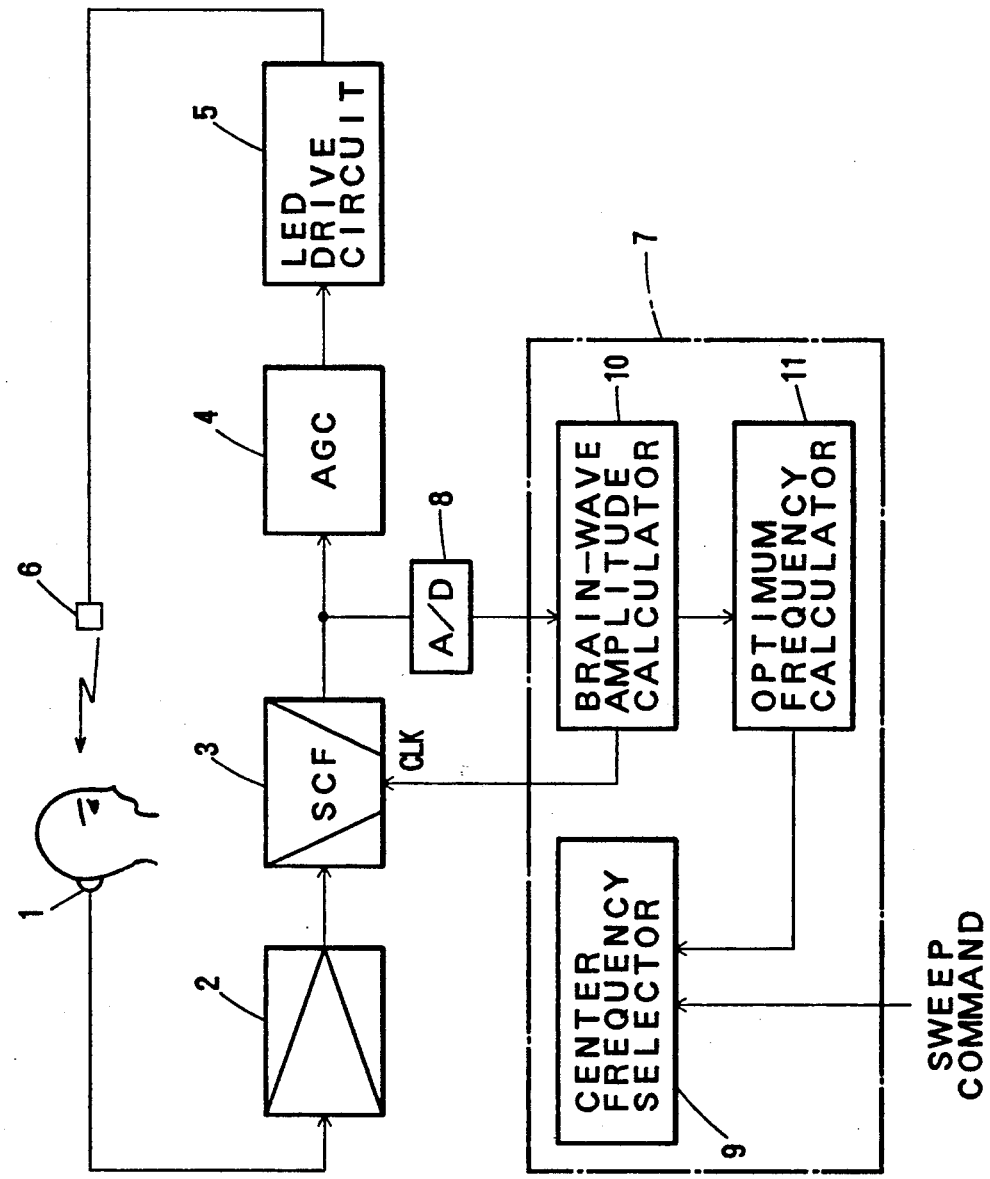
FIG. 1 is a block diagram showing an embodiment of a brain wave inducing apparatus according to the invention.

FIG. 1 is a block diagram showing an embodiment of a brain wave inducing apparatus according to the invention. In the figure, a brain wave sensor 1 picks up the brain waves from a human body or testee. A brain wave amplifier 2 amplifies the brain waves picked up by means of the brain wave sensor 1 to a signal level sufficient for subsequent brain wave processing. A band-pass filter 3 receives the output of the brain wave amplifier 2 and passes only selected frequency components. The band pass filter 3 has a variable center frequency and takes the form of a switched capacitor filter (SCF) whose center frequency is changed in accordance with the frequency of a clock CLK supplied thereto. An automatic gain control (AGC) circuit 4 receives the output of band pass filter 3 and automatically maintains the amplitude of the brain wave outputted from the filter 3 at a predetermined constant level. An LED drive circuit 5 drives a light emitting diode (LED) 6 to cycle on and off in accordance with the brain wave inducing signal outputted from the automatic gain control circuit 4. The blinking light from the LED 6 is fed to the testee so as to stimulate the testee to induce a desired brain wave from the testee.

A microcomputer 7 includes primarily a CPU, ROM, RAM which form together with a built-in program a center frequency selector 9 and brain wave amplitude calculator 10, and optimum frequency calculator 11. The microcomputer 7 receives signals from the band pass filter 3 via an A/D converter 8.

The brain amplitude calculator 10 calculates and stores therein the amplitudes of outputs of the band pass filter 3 for the respective center frequency selected by the center frequency selector 9 as the selector 9 changes the center frequency of the band pass filter 3 to sweep across the frequency range of a desired brain wave. The optimum frequency calculator 11 performs calculation on the basis of the amplitudes of respective center frequencies stored in the brain amplitude calculator 10 so as to determine the center frequency of the band pass filter 3 that is optimal for inducing a desired brain wave. The calculated optimum frequency of the band pass filter 3 is outputted to the center frequency selector 9. The center frequency selector 9 controllably changes the center frequency fo of the band pass filter 3 by changing the frequency of the clock CLK.

Operation

Figure 2:
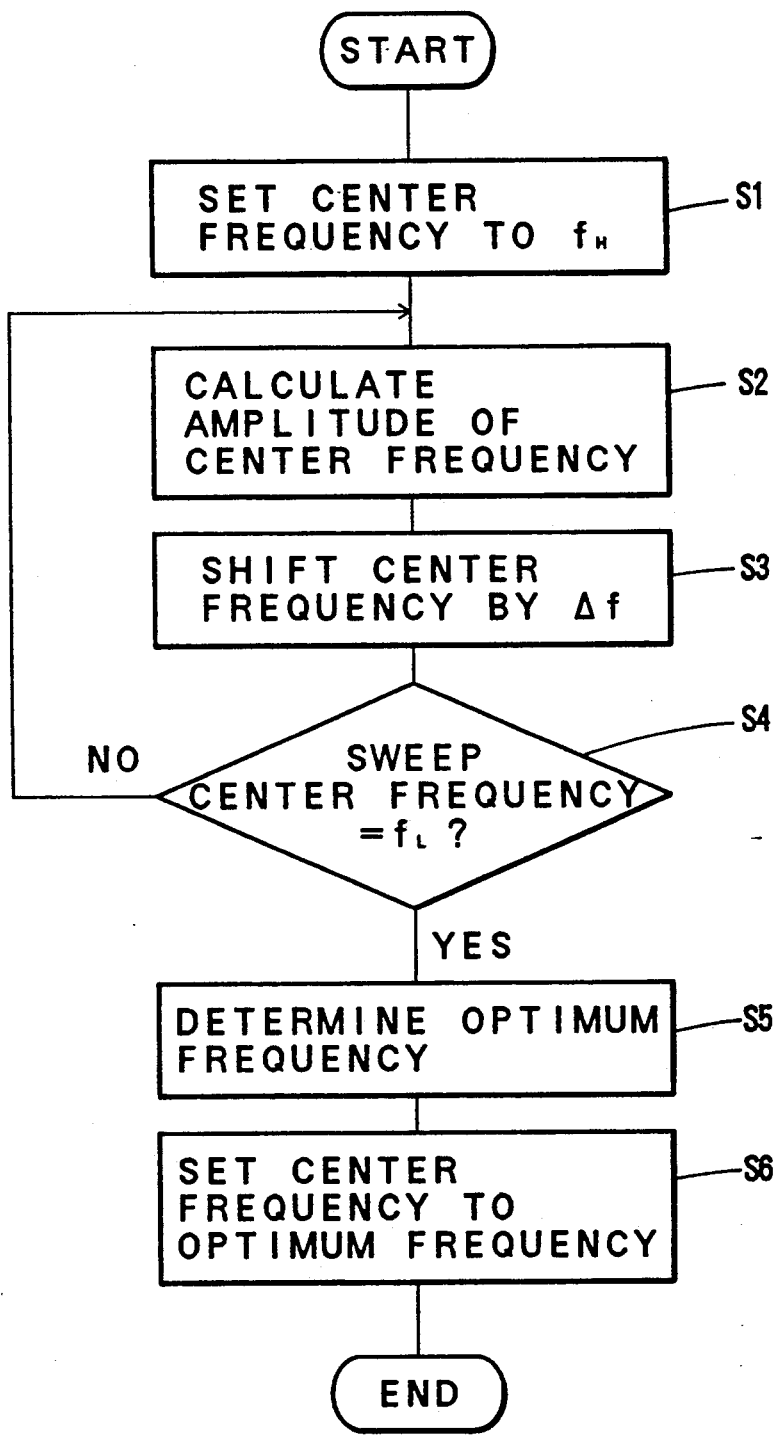
FIG. 2 is a flowchart of the embodiment in FIG. 1.
Figure 3:
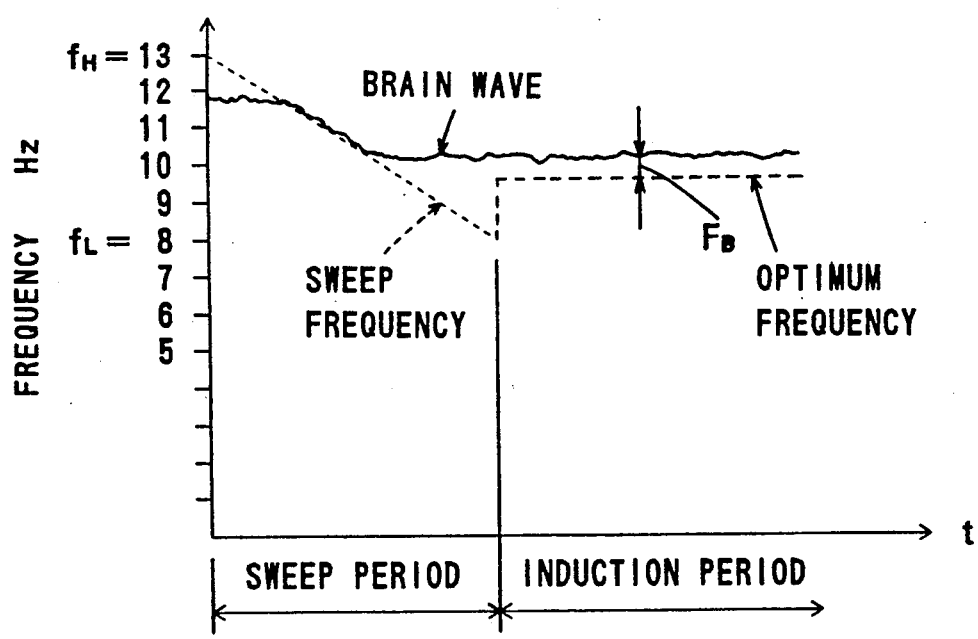
FIG. 3 shows swept center frequencies of the band pass filter and brain waves induced correspondingly when inducing an a brain wave.

The operation of the aforementioned embodiment will now be described with reference to FIG. 2 which shows a flowchart of the apparatus of the invention and FIG. 3, which shows an induced α brain wave and the center frequency of the band-pass filter 3 during the sweeping of the center frequency and as well as during induction of α wave.

At step 1, when a sweep-start command is supplied from an external circuit, the center frequency selector 9 outputs the clock CLK indicative of an appropriate upper limit frequency fH of the center frequency e.g., fH=13 Hz for an α wave. Then, the center frequency of the band-pass filter 3 is swept starting from fH=13 Hz as shown in FIG. 3.

At step 2, the brain wave amplitude calculator 10 calculates the output of the band pass filter 3 now having a center frequency fH=13 Hz, and stores the center frequency F(=13 Hz) and the calculated amplitude A into an internal memory.

At step 3, the center frequency selector 9 shifts the center frequency to the lower side by Δf from fH=13 Hz, so that the center frequency of the band-pass filter is now fH-Δf.

At step 4, it is determined whether the new center frequency is below a lower limit frequency fL of the band-pass filter. For example, fL=8 Hz for an α wave. If the answer is NO, then the program returns to step 2; if YES, then the program proceeds to step 5. In this manner, the aforementioned steps 2-4 are iteratively carried out for frequencies fH=13 to 8 Hz as depicted by a dotted line in FIG. 3, so that the amplitudes of the output of the band pass filter 3 for the respective center frequencies are stored into the internal memory of the brain wave amplitude calculator 10.

At step 5, when the sweep operation from fH=13 to 8 Hz has completed, the optimum frequency calculator 11 reads out the respective sweep center frequency Fi and amplitude thereof Ai stored in the brain wave amplitude calculator 10, and calculates an optimum center frequency fo for inducing a desired brain wave as follows:

$$fo = \left(\sum_{i=1}^{i=n} Ai\,Fi \Big/ \sum_{i=1}^{i=n} Ai\right) \pm FB \quad (1)$$

where Fi is an ith swept center frequency, Ai is the amplitude of the ith swept center frequency Fi, i is an integer from 1 to n, and FB is a bias frequency.

The first term of on the right side of equation (1) is a weighted average frequency of brain waves in the swept frequency range (fH to fL) and the second term is a bias frequency for efficiently inducing a desired brain wave.

Brain waves have a "pull-in" phenomenon. In other words, a brain wave inducing signal having a frequency slightly lower than a desired brain wave is more effective in directing the testee into relaxation. On the other hand, a brain wave inducing signal having a frequency slightly higher than a desired brain wave is more effective in directing the testee into an alert, active condition. Thus, equation (1) takes the pull-in phenomenon into account to calculate the optimum center frequency.

At step 6, the optimum frequency calculator 11 sends a command indicative of the optimum center frequency fo to the center frequency selector 9. Then, the center frequency selector 9 sends the clock CLK corresponding to the command from the optimum frequency calculator 11 to the band pass filter 3 to set the filter 3 for the calculated optimum frequency fo. Thus, a desired brain wave is efficiently induced in accordance with the calculated optimum center frequency. FIG. 3 shows a graph when the bias frequency in equation (1) is -FB.

While the aforementioned embodiment has been described with respect to the induction of an α wave, the invention may of course equally be applied to induce a θ wave and a β wave. The sweep range is set to 4-7 Hz for a θ wave and 13-30 Hz for a β wave. If the bias frequency FB in equation (1) is not necessary, only the first term may be used to calculate the optimum center frequency.

What is claimed is:

1. A brain wave inducing apparatus, in which the brain waves of a testee are first subjected to filtering to provide a brain wave inducing signal having an optimum frequency for inducing a desired brain wave and in which the testee is optically stimulated by the brain wave inducing signal, comprising;
   a band pass filter, having a variable center frequency, for outputting a selected frequency component of said brain waves based on a selected center frequency said center frequency being varied in accordance with a signal supplied thereto, in order to sweep across a frequency of brain waves of the testee;
   a brain wave amplitude calculator for calculating and storing therein each selected center frequency and each corresponding amplitude of the output of said band pass filter;
   an optimum frequency calculator for calculating and outputting a command indicative of an optimum center frequency of said band pass filter based on the center frequencies and corresponding amplitudes stored by the brain wave amplitude calculator; and
   a center frequency selector for changing the center frequency of said band pass filter in accordance with the command from said optimum frequency calculator.

2. A brain wave inducing apparatus according to claim 1, wherein said center frequency selector sets an upper limit of a frequency range of a desired brain wave as an initial center frequency of said band pass filter when activated by an external command, and repeatedly decreases the center frequency by a predetermined amount until the center frequency equals a lower limit, said brain wave amplitude calculator calculating and storing a current central frequency and amplitude each time the central frequency is decreased.

3. A brain wave inducing apparatus according to claim 1, wherein said band pass filter is a switched capacitor filter.

4. A brain wave inducing apparatus according to claim 1, wherein said optimum center frequency fo of said band pass filter is calculated based on the following equation:

$$fo = \left(\sum_{i=1}^{i=n} Ai\,Fi \Big/ \sum_{i=1}^{i=n} Ai\right)$$

wherein i is from 1 to n, Fi is an ith center frequency of said band pass filter, Ai is an amplitude of the ith center frequency Fi component from the band pass filter.

5. A brain wave inducing apparatus according to claim 1, wherein, when a desired brain wave is an α wave, said ith center frequency is calculated by the following equation:

$$fo = \left(\sum_{i=1}^{i=n} Ai\,Fi \Big/ \sum_{i=1}^{i=n} Ai\right) - FB$$

where i is from 1 to n, Fi is an ith center frequency of said band pass filter, Ai is an amplitude of the ith center frequency Fi component from the band pass filter and FB is a bias frequency.

6. A brain wave inducing apparatus according to claim 1, wherein, when a desired brain wave is an $\beta$ wave, said ith center frequency is calculated by the following equation:

$$fo = \left(\sum_{i=1}^{i=n} Ai\,Fi \Big/ \sum_{i=1}^{i=n} Ai\right) - FB$$

where i is from 1 to n, Fi is an ith center frequency of said band pass filter, Ai is an amplitude of the ith center frequency Fi component from the band pass filter and FB is a bias frequency.

7. A brain wave inducing apparatus according to claim 1, wherein said output of said band pass filter is converted into an optical signal by a light emitting diode.

8. A brain wave inducing apparatus according to claim 1, wherein said center frequency selector, when obtaining said optimum center frequency, sets said center frequency of said band pass filter at a first frequency limit and repeatedly shifts said center frequency by an incremental amount until said center frequency equals a second frequency limit, in order to allow said band pass filter to output multiple frequency components between said first and second frequency limits, thereby scanning the brain wave of the testee.

9. A brain wave inducing apparatus according to claim 8, wherein said optimum frequency calculator calculates said optimum center frequency after said center frequency is shifted to said second frequency limit, said center frequency selector setting said center frequency equal to said optimum center frequency calculated by said optimum frequency calculator.

10. A brain wave inducing apparatus according to claim 1, wherein said brain wave amplitude calculator calculates a center frequency and corresponding amplitude of the output of said band pass filter for each selected center frequency, said optimum frequency calculator calculating said optimum center frequency once said brain wave amplitude calculator calculates all of said selected center frequencies.

11. A brain wave inducing apparatus of a type that calculates an optimum frequency for a brain wave inducing signal for a testee by scanning a frequency range of brain waves of said testee and that stimulates the testee with said brain wave inducing signal, said apparatus comprising:

filter means, having a variable center frequency, for outputting a selected frequency component of said brain wave based on a selected center frequency for said filter means, amplitude calculator means, connected to said filter means, for calculating a center frequency and an amplitude of an output signal from said filter means, selector means, connected to said filter means, for incrementally shifting the selected center frequency of said filter means in order to scan said brain wave frequency range and obtain said optimum center frequency.

12. A brain wave inducing apparatus according to claim 11, further comprising:

frequency calculator means, connected between said amplitude calculator means and said selector means, for calculating an optimum center frequency based on all of the calculated center frequencies and corresponding amplitudes, said selector means incrementally shifting the selected center frequency from a first frequency limit by a predetermined amount until the selected center frequency equals a second frequency limit, said selector means setting the selected center frequency equal to the optimum center frequency calculated by said frequency calculator means.

13. A brain wave inducing apparatus, according to claim 11, wherein said selector means sets said center frequency of said filter means at an upper limit while said amplitude and frequency calculator means calculate said center frequency, the corresponding amplitude and said optimum center frequency.

14. A brain wave inducing apparatus, according to claim 13, further comprising:

memory for storing each center frequency and amplitude calculated by said amplitude calculator means.

15. A brain wave inducing apparatus according to claim 11, wherein said selector means, when obtaining said optimum center frequency, sets said center frequency of said filter means at a first frequency limit and repeatedly shifts said center frequency by an incremental amount until said center frequency equals a second frequency limit, in order to allow the filter means to output multiple frequency components between said first and second frequency limits.

16. A brain wave inducing apparatus according to claim 15, wherein said frequency calculator means calculates said optimum center frequency after said center frequency is shifted to said second frequency limit, said selector means setting said center frequency equal to said optimum center frequency calculated by the frequency calculator means.

17. A brain wave inducing apparatus according to claim 11, wherein said amplitude calculator means calculates a center frequency and corresponding amplitude of the output of said filter means for each selected center frequency, said frequency calculator means calculating the optimum center frequency once said amplitude calculator means calculates all of said selected center frequencies.

* * * * *